Jan. 15, 1935. W. M. ELMER Plant Pat. 117
ROSE
Filed May 25, 1934
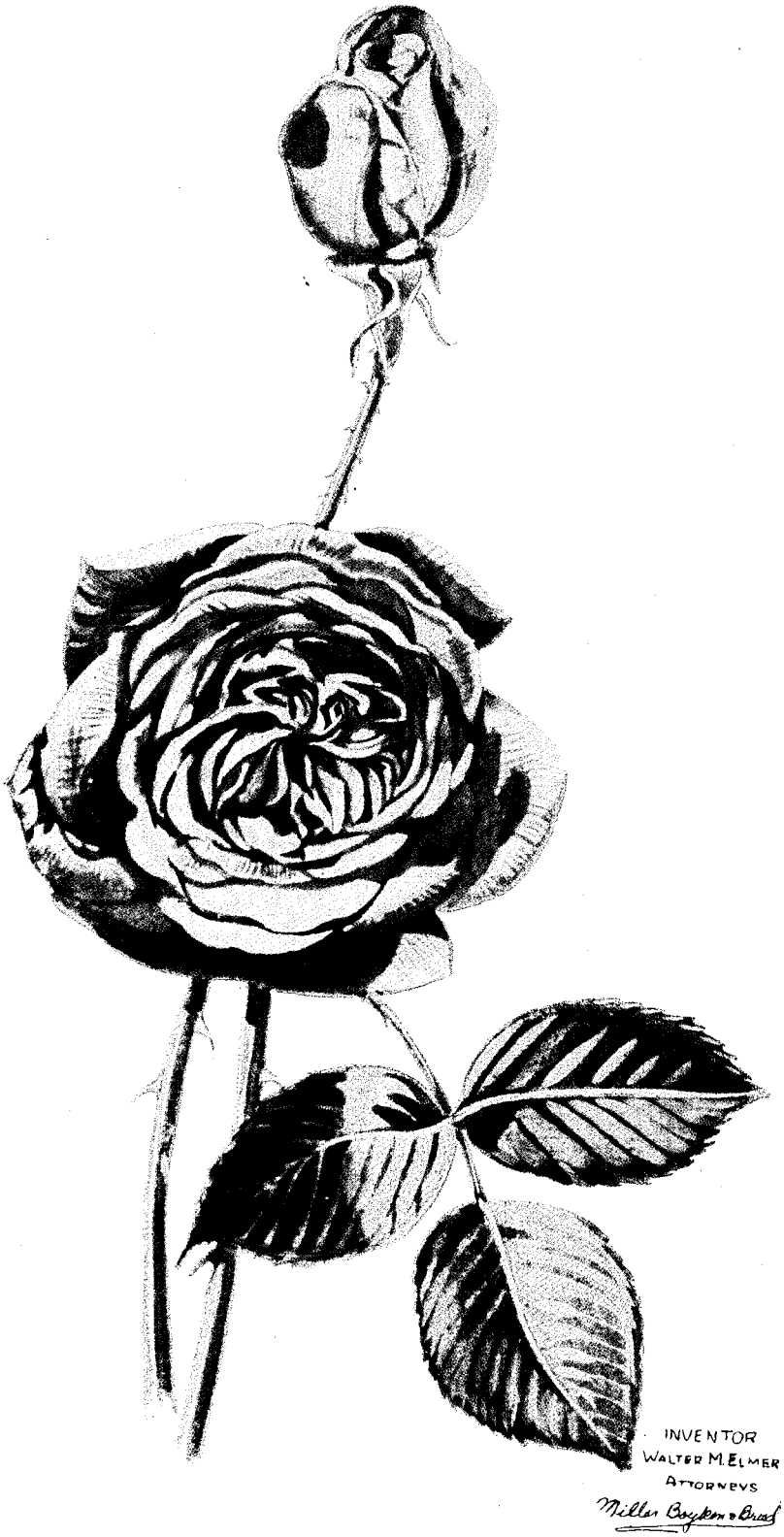

Patented Jan. 15, 1935

Plant Pat. 117

UNITED STATES PATENT OFFICE

117

ROSE

Walter M. Elmer, San Jose, Calif., assignor to
Andrew J. Elmer, San Jose, Calif.

Application May 25, 1934, Serial No. 727,435

1 Claim. (Cl. 47—61)

This invention relates to roses, and the object of the invention is to produce a continuous blooming, rapid-growing, climbing hybrid tea rose that blooms in profusion on the new wood or the first year after budding. Other objects will appear in the specification attached hereto.

The colored drawing accompanying this application shows a bud and a substantially fully developed rose with stems attached and a portion of the foliage.

The rose and the plant bearing it originated as a sport of the bush rose known as the "E. G. Hill" hybrid tea rose and was discovered at San Jose, Santa Clara County, California, and has been, and is, asexually reproduced as a distinct and new variety of a climbing hybrid tea rose by budding. The varietal characteristics which distinguish my plant from the parent varieties have been observed upon buds or plants asexually propagated from the original sporting branch or plant. The flower is of a rich permanent crimson to alizarin crimson, changing to light purple lake with age, except the very tightly packed middle area of the outer petals which become lighter with age than the marginal areas. The buds are relatively longer than most varieties and the stems are from eight inches to sixteen inches in length with one rose to a stem. When fully opened, the flowers are from three to five inches in diameter more or less.

Two or three characteristics in particular distinguish my rose from other roses in addition to its being a climbing rose in which the color and shape of the blossom have the characteristics of the "E. G. Hill" bush rose.

Firstly, the plant is a continuous bloomer the year round provided the temperature does not drop to substantially freezing for an extended period of time, and it is supplied with moisture.

Secondly, my plant is a climber that blooms profusely on the new wood, or on first year growth, in contra-distinction to ordinary climbers that delay blooming until the second year.

Thirdly, the plant is an exceptionally fast grower, and commences blooming within about thirty days after the budded shoot has commenced to grow and at the end of sixty days the plant attains a height of about six feet and is covered with flowers.

In summary of the foregoing, the novelty in my rose resides in the fact that it is an exceptionally fast-growing climbing rose bearing a profusion of long-stemmed large flowers having substantially the color characteristics of the flowers shown in the drawing, and which rose blooms continuously the year round, said flowers being produced on new or first year wood. The colors specified in the foregoing and general description and following detailed description have been carefully checked with the colors as presented in the charts in "Specimen Tints of Artists Colours," published by Winsor & Newton, Ltd., London.

The following is a detailed description of my rose, plant and flower:

Parentage:—
Sport from "E. G. Hill" rose.

Classification:—
Climbing Rose.

*Flower*

Blooming habit:—
Recurrent—everblooming.

Bud:—
*Size.*—Medium.
*Form.*—Pointed but not slender.
*Color.*—Deep purple lake.
*Sepals.*—Color; light cinnabar green; shape, ovate-lanceolate at base, long attenuate at apex often broadened slightly before tip and with few to several long slender teeth; position, turned forward over petals (in full bloom flower turned abruptly backward).
*Calyx.*—Shape; short campanulate; size, small; aspect, smooth.
*Peduncle.*—Medium to long with a sparse scattering of small weak prickles.
*Opening.*—Opens well, does not ball.

Bloom:—
*Size.*—Medium to large (4½ to 5 inches).
*Borne.*—Singly or with one or two accessory blossoms borne several inches below the terminal one.
*Stems.*—Medium size to stoutish; flexible but sturdy.
*Form.*—With high pointed center at first, rounded when open with outer petals turned back in outer half.
*Petalage.*—50 to 65, innermost small and crowded.
*Color.*—Rich permanent crimson to alizarin carmine, changing to light purple lake with age, (except the very tightly packed center petals which are burnt carmine) middle area of outer petals become lighter with age than the marginal areas. Veins in all petals slightly darker at all ages than rest of petal.
*Discoloration.*—The color becomes darker each day until the petals fall.
*Texture.*—Firm and strong but not heavy.
*Appearance.*—Inside velvety, outside slightly metallic.
*Form.*—Urn-shaped to open campanulate as flower opens.
*Arrangement.*—Petals uniformly disposed except in center where they are crowded and folded in groups.
*Persistence.*—Drop off cleanly.
*Fragrance.*—Pronounced and rich.
*Lastingness.*—Greater than average, blooms last several days.

Genital organs:—
Stamen filaments pink, anthers orange yellow.
*Color.*—Pollen, yellow.
*Styles.*—Light carmine, styles in bunches and of unequal length.
*Stigmas.*—Pale orange madder.
*Ovaries.*—Some normal others abortive.
Fruit:—
*Size.*—Large.
*Form.*—Globose pear-shaped.
*Seed.*—18 to 21.
*Color.*—Dark green.

*Plant*

Form:—
*Growth.*—Active and sturdy.
Foliage:—
*Size.*—Medium.
*Quantity.*—Moderate.
*Color.*—Mature foliage: medium dark bluish green with suggestions of purple on margins; below, same but paler.
*Shape.*—Of leaf and leaflets, ovate, tips of leaflets acuminate.
*Texture.*—Of medium firmness, somewhat crisp.
*Edge.*—Serrate.

Leaf stem:—
*Color.*—Green to green overlaid with purple.
*Structure.*—Smooth beneath, or with small prickles sparingly present, with weak hair-like prickles above between the leaflets.
*Stipules.*—Medium sized, oblong to ovate-oblong, with long tapering tips.
*New wood.*—Bluish green and slightly glaucous.
*Old wood.*—Bluish to yellowish green, glossy where glaucous covering has worn away.
Thorns:—
*Quantity.*—Moderate, less numerous on flower bearing stems.
*Form.*—Base thin and narrow, point sharp and slender, definitely recurved.
*Color.*—When young, rose pink over yellow.
*Position.*—Irregular, ½ to 3 inches apart.

Having described my rose, I claim:

The new variety of rose plant as disclosed, characterized by a fast-growing, continuous-blooming climbing plant producing relatively large double flowers on first year growth which flowers are substantially identical to the flowers of the E. G. Hill bush rose in shape, size and color.

WALTER M. ELMER.